United States Patent
Klomp

(10) Patent No.: US 10,327,949 B2
(45) Date of Patent: Jun. 25, 2019

(54) DEVICE FOR CONTROLLING THE IRRIGATION PRESSURE

(71) Applicant: EOS GmbH, Eschweiler (DE)

(72) Inventor: Manfred Klomp, Hulsberg (NL)

(73) Assignee: EOS GMBH, Eschweiler (DE)

( * ) Notice: Subject to any disclaimer, the term of this patent is extended or adjusted under 35 U.S.C. 154(b) by 783 days.

(21) Appl. No.: 14/844,756

(22) Filed: Sep. 3, 2015

(65) Prior Publication Data
US 2016/0100981 A1 Apr. 14, 2016

(30) Foreign Application Priority Data

Oct. 10, 2014 (EP) .................................... 14188393

(51) Int. Cl.
*A61M 35/00* (2006.01)
*A61F 9/007* (2006.01)
(Continued)

(52) U.S. Cl.
CPC ....... *A61F 9/00736* (2013.01); *A61M 3/0216* (2014.02); *A61M 3/0237* (2013.01);
(Continued)

(58) Field of Classification Search
CPC ... A61F 9/00736; A61F 9/007; A61M 3/0216; A61M 3/0237; A61M 39/223; A61M 39/24
See application file for complete search history.

(56) References Cited

U.S. PATENT DOCUMENTS

| | | |
|---|---|---|
| 1,956,006 A | 4/1934 | Coons |
| 5,032,111 A | 7/1991 | Morris et al. |
| | (Continued) | |

FOREIGN PATENT DOCUMENTS

| | | |
|---|---|---|
| EP | 0717970 | 6/1996 |
| WO | WO2009017921 | 2/2009 |
| WO | WO2011105909 | 9/2011 |

OTHER PUBLICATIONS

European Search Report dated Apr. 21, 2015 issued for European Patent Application 14188393.4.

*Primary Examiner* — Ariana Zimbouski
(74) *Attorney, Agent, or Firm* — Workman Nydegger

(57) ABSTRACT

A device including a gas pressure device providing a variable initial pressure ($P_A$), a fluid container providing a fluid for rinsing an eye, the fluid container being connected to a surgical handpiece to deliver the fluid into the eye at an irrigation pressure ($P_I$) predeterminable by the surgeon. The fluid container is connected to a connecting element on a side which is upper in the operating position, and the fluid container communicates with a gas phase container via a mandrel of the connecting element on a lower side of the gas phase container, and the gas phase container and/or the fluid container exhibit(s) a gas phase and the gas phase communicates with the gas pressure device via the connecting element or a fluid container line, and the irrigation pressure ($P_I$) of the surgical handpiece is adjustable via the variable initial pressure ($P_A$) of the gas pressure device.

11 Claims, 5 Drawing Sheets

(51) Int. Cl.
*A61M 3/02* (2006.01)
*A61M 39/22* (2006.01)
*A61M 39/24* (2006.01)

(52) U.S. Cl.
CPC .......... *A61M 39/223* (2013.01); *A61M 39/24* (2013.01); *A61M 2039/229* (2013.01); *A61M 2205/3331* (2013.01); *A61M 2210/0612* (2013.01)

(56) References Cited

U.S. PATENT DOCUMENTS

| | | | | |
|---|---|---|---|---|
| 5,084,035 | A * | 1/1992 | Salvadori | A61F 5/4407 604/322 |
| 5,360,398 | A * | 11/1994 | Grieshaber | A61M 1/0058 604/30 |
| 5,533,647 | A * | 7/1996 | Long-Hsiung | A61M 5/162 222/83 |
| 2002/0040206 | A1* | 4/2002 | Heil | A61J 1/2096 604/202 |
| 2013/0123680 | A1* | 5/2013 | Ha | A61M 3/0241 604/22 |
| 2013/0131578 | A1* | 5/2013 | Stalmans | A61F 9/00736 604/22 |
| 2013/0331811 | A1* | 12/2013 | Butterfield | A61M 5/1408 604/500 |
| 2015/0351965 | A1* | 12/2015 | Umentum | A61F 9/04 221/92 |

\* cited by examiner

DEVICE FOR CONTROLLING THE IRRIGATION PRESSURE

The present application claims priority to European Patent Application No. 14188393.4, filed with the European Patent Office on Oct. 10, 2014, entitled "Device for Controlling the Irrigation Pressure", which is hereby incorporated by reference in its entirety.

The invention relates to a device for use in eye surgery comprising a gas pressure device for providing a variable initial pressure, a fluid container for providing a fluid for rinsing an eye, wherein the fluid container is connected to a surgical handpiece on a side which is lower in the operating position in order to deliver the fluid into the eye at an irrigation pressure predeterminable by the surgeon.

Document U.S. Pat. No. 5,032,111 discloses such a device which is part of an ocular surgical device and by means of which the lens of a patient's eye can be removed. During the surgery, at first a cut is placed on the eye by the surgeon, via which the old lens, which has been divided into small pieces, is removed. In order to facilitate the removal of the small pieces of the old lens and to prevent the volume in the eye originally occupied by the old lens from collapsing during the surgery, the fluid must be delivered from the surgical handpiece into the eye on which surgery has been performed at an irrigation pressure. An irrigation pressure which is too high would permanently damage the eye, and at an irrigation pressure which is too low the eye is in danger of collapsing, for which reason the surgeon has to be able to adjust the appropriate irrigation pressure. For this purpose, a flexible line is formed between the fluid container and the surgical handpiece. Furthermore, the fluid container is connected to the gas pressure device via a further line, the latter is designed for controlling the irrigation pressure via the gas pressure device. For this control, the initial pressure can be lowered or increased at the control device, this bidirectional pressure regulation of the initial pressure requires that the line between the gas pressure device and the fluid container carries only gas. For this purpose, the end of the line which is located in the interior of the fluid container comprises a long pipe ending in the gas phase of the fluid container. For connecting the fluid container to the gas pressure device, the sealing of the fluid container is broken with the pipe.

It has turned out to be disadvantageous that the required length of said pipe adversely impedes the establishment of the connection and the breaking of the sealing. A shorter pipe would indeed facilitate handling, but fluid would also be able to penetrate into the line between the gas pressure device and the fluid container. Thereby, the gas pressure device might sustain damage or, respectively, the bidirectional pressure regulation between the gas pressure device and the fluid container and, hence, the control of the irrigation pressure might be impossible.

The invention is based on the object of providing a device for use in eye surgery which, provided that the bidirectional pressure regulation persists, facilitates the connection of the fluid container to the gas pressure device for a user.

According to the invention, this problem is solved in that the fluid container is connected to a connecting element on a side which is upper in the operating position, wherein the fluid container communicates with a gas phase container via a mandrel of the connecting element on a lower side of the gas phase container and wherein the gas phase container and/or the fluid container exhibit(s) a gas phase and the gas phase communicates with the gas pressure device via the connecting element or a fluid container line, whereby the irrigation pressure $P_I$ of the surgical handpiece is adjustable via the variable initial pressure $P_A$ of the gas pressure device.

As a result, the advantage is obtained that the connection between the gas phase and the gas pressure device can be established without any bulky components and the bidirectional pressure regulation between the fluid container and the gas pressure device will persist. For this purpose, the connection between the gas pressure device and the fluid container is enlarged by the gas phase container. With the gas phase container, the fluid is provided for the surgical procedure. During the pre-surgery preparation, the fluid is drained into the fluid container in fact to such an extent that either the end part of the line between the gas pressure device and the gas phase container projects in the gas phase container into the gas phase above the fluid level or, as in the preferred exemplary embodiment, the gas phase in the fluid container communicates with the gas pressure device via the fluid container line. Thereby, the end part of the line may advantageously be formed from a short pipe or a mandrel, and via the corresponding gas-carrying line, the irrigation pressure can be controlled by the variable initial pressure of the gas pressure device. By reducing or increasing the initial pressure, also the irrigation pressure is lowered or raised.

By subsequently venting the line between the fluid container and the surgical handpiece by means of the fluid, the fluid is provided at the surgical handpiece.

Further advantageous embodiments of the device according to the invention are explained in further detail below on the basis of the figures.

Figure 1:
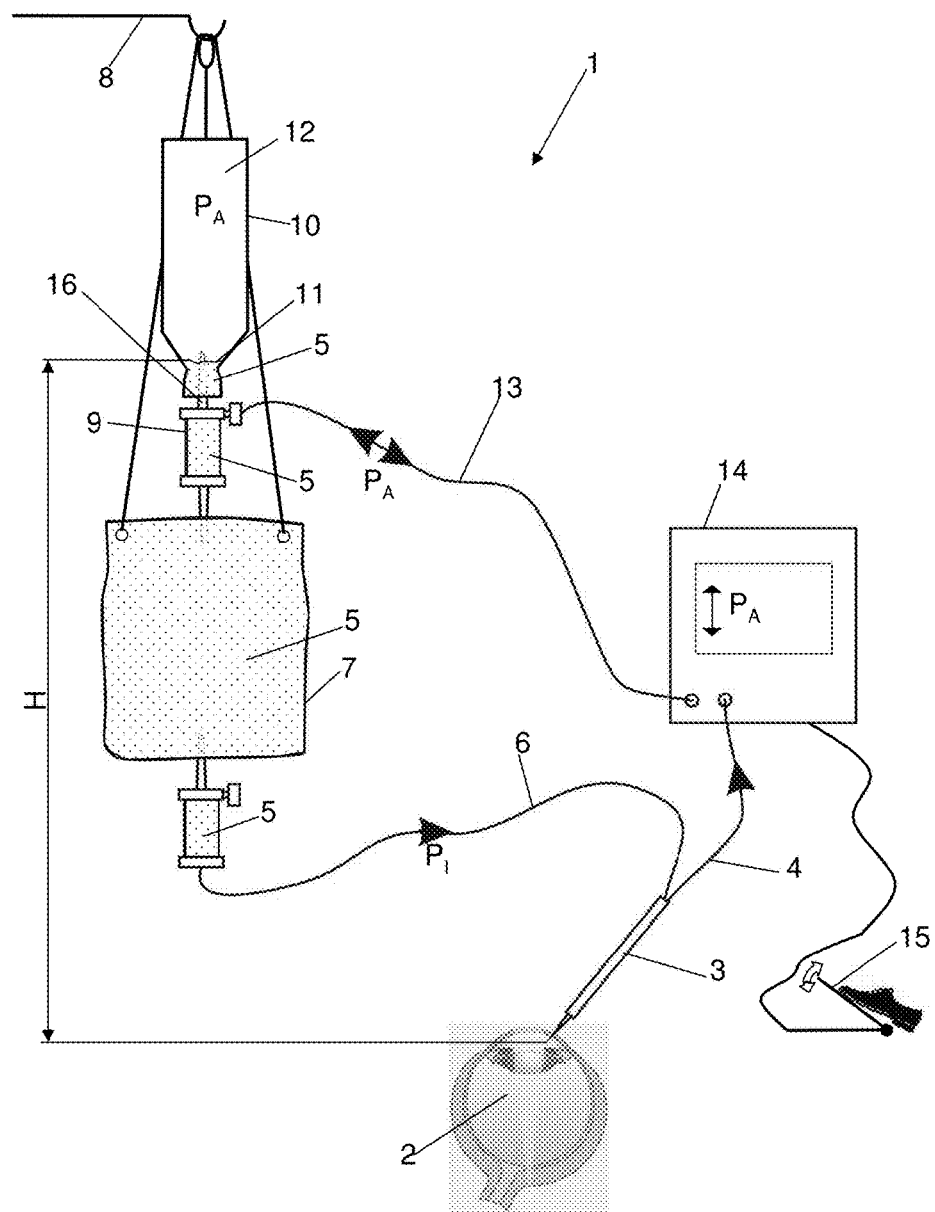
FIG. 1 shows a schematic design of a device according to the invention.

FIG. 1 shows a schematic design of a device 1 for use in eye surgery, with an eye 2 to be treated into which a surgical handpiece 3 is inserted via an operational aperture. The surgical handpiece 3 comprises a cutting device located at the end of the surgical handpiece 3 in the interior of the eye 2. Said cutting device serves for detaching eye tissue which is rinsed out of the eye 2 via a line located in the surgical handpiece 3 and leading to a line 4. For this rinsing process, a fluid 5 at an irrigation pressure $P_I$ is provided in the eye 2 via the surgical handpiece 3. For this purpose, the surgical handpiece 3 is connected to a fluid container 7 via a line 6, wherein the fluid container 7 is suspended from an infusion holder 8 and filled with the fluid 5. At an upper end, the fluid container 7 is connected via a connecting element 9 to a gas phase container 10, which is also suspended from the infusion holder 8. A fluid level 11 is the boundary between the fluid 5 and a gas phase 12. Via the connecting element 9 and via a line 13, the gas phase 12 communicates with a gas pressure device 14. The gas pressure device 14 is composed of a gas pump and a control system for generating a variable initial pressure $P_A$. The control system for the desired initial pressure $P_A$ is actuated via a foot pedal 15 which is operated by the surgeon. Via the line 13, the adjusted initial pressure $P_A$ also prevails in the gas phase 12. The irrigation pressure $P_I$ results from the sum of the hydrostatic pressure over a height H and the adjustable initial pressure $P_A$. Thus, the required irrigation pressure $P_I$ is also controlled via the foot-operated control of the initial pressure $P_A$.

It may be mentioned that the gas phase container 10 is configured by a commercially available bottle filled with a saline solution. Said bottle is a common product for the medical field. Furthermore, the connecting element may comprise a mandrel of a commercially available infusion device, wherein a commercially available infusion device is understood to be, for example, the product Intrafix® SafeSet of the Braun company. In this way, the advantage is obtained that, by using standardized commercially available products, the handling is substantially facilitated for a user on the one hand and, on the other hand, the costs for the device can thus be reduced.

Figure 2:
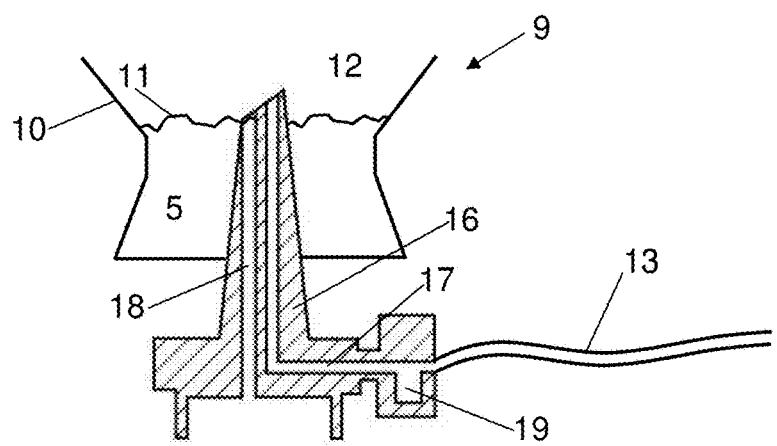
FIG. 2 shows a partial view of the connecting element of the device according to the invention of FIG. 1, wherein the connecting element is depicted in a sectioned way.

FIG. 2 shows an upper section of the connecting element 9 of the device 1 according to the invention in accordance with FIG. 1. The connecting element 9 comprises a mandrel 16 in which a first channel 17 and a second channel 18 are provided. The first channel 17 and the line 13 connect the gas phase container 10 to the gas pressure device 14. On the first channel 17, a fluid deposition device 19 is designed which is configured for protecting the gas pressure device 14 from unwanted fluid entries. A fluid 5 which, optionally, enters from the gas phase container 10 into the first channel 17 at a reduced initial pressure $P_A$ is collected in the fluid deposition device 19 as a result of gravity, whereas the gas at the initial pressure $P_A$ is able to flow from the gas pressure device 14 unhindered past the fluid deposition device 19. The second channel 18 connects the gas phase container 10 to the fluid container 7. In the device 1 according to FIG. 1 and FIG. 2, the bidirectional pressure regulation requires protection from fluid entries, which protection also enables a bidirectional conduction of gas. Hence, the use of a one-way valve, which prevents fluid entries in line 13, is not target-aimed in said exemplary embodiment.

FIG. 1 and FIG. 2 show the device 1 upon completion of the pre-surgery preparation which consists essentially of the following procedural steps. The sealed gas phase container 10 is filled with the fluid 5 and is suspended from the infusion holder 8. By means of the connecting element 9, the gas pressure device 14 is connected, during the pre-surgery preparation, to the gas phase container 10 via the first channel 17 and the gas phase container 10 is connected to the fluid container 7 via the second channel 18. The connection is established with the mandrel 16 by means of which the sealing of the gas phase container 10, which is not illustrated, is broken. In order to control the irrigation pressure $P_I$ during the surgical procedure, the first channel 17 must end in the gas phase 12. For this purpose, the fluid 5 is started to be drained from the gas phase container 10 into the fluid container 7 according to the method of the invention. During the draining, the fluid container 7 is filled with the fluid 5 via the second channel 18, whereby the negative pressure emerging in the gas phase container 10 is equalized through the first gas-carrying channel 17. After the fluid 5 has been drained completely into the fluid container 7, the gas pressure device 14 is directly connected to the gas phase 12 and the fluid container 7 can be charged with the initial pressure $P_A$. Subsequently, the fluid 5 is made available at the surgical handpiece 3 at the irrigation pressure $P_I$. By means of the bidirectional regulation of the initial pressure $P_A$, the irrigation pressure $P_I$ can advantageously be increased or lowered particularly quickly, depending on the surgeon's requirement.

Figure 3:
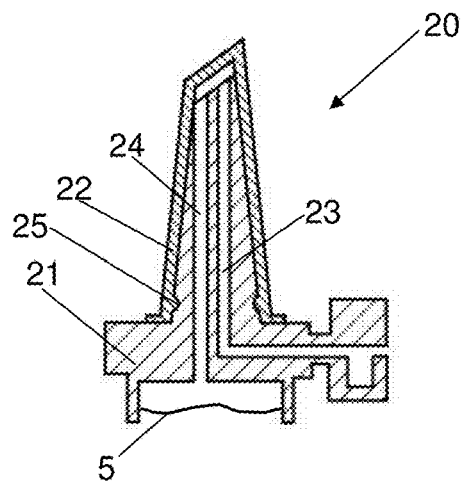
FIG. 3 shows a partial view of a connecting element comprising a covering means of a device according to the invention, wherein the connecting element is depicted in a sectioned way.

FIG. 3 shows an upper section of a connecting element 20 of a device according to the invention, which may also be used in the device 1 instead of the connecting element 9. The connecting element 20 comprises a mandrel 21 and a covering means 22. A first channel 23 and a second channel 24 extend inside the connecting element 20. On the connecting element 20 and on the covering means 22, a gastight elastic locking seal 25 is configured for connecting the first channel 23 to the second channel 24 in a gastight manner.

The pre-surgery preparation for the exemplary embodiment according to FIG. 1 with the connecting element 20 according to FIG. 3 is, apart from an additional procedural step, in line with the description of FIG. 1 and FIG. 2. The additional procedural step exists due to the fact that, after the fluid 5 has been drained from the gas phase container 10 into the fluid container 7, the gas phase container 10 is separated from the connecting element 20 and, thereafter, the connecting element 20 is covered with the covering means 22. By separating the gas phase container 10, the volume of the gas phase 12 is reduced, whereby also less gas has to be compressed or expanded for the regulation, depending on the initial pressure $P_A$ which has been adjusted. Thus, the inertia of the irrigation pressure control is advantageously reduced, whereby the irrigation pressure $P_I$ as desired by the surgeon is provided at the handpiece 3 particularly quickly and without any time delay with a change in the position of the foot pedal 15.

Figure 4:
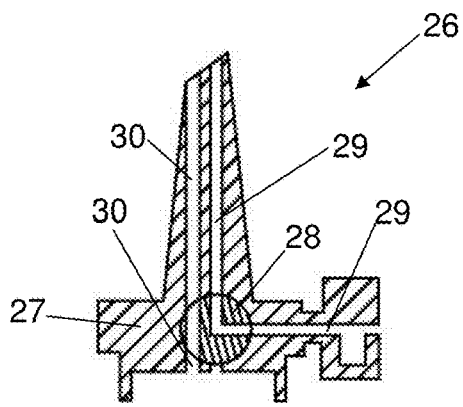
FIG. 4 shows a partial view of a connecting element comprising a three-way stopcock of a device according to the invention, wherein the connecting element is depicted in a sectioned way.

FIG. 4 shows an upper section of a connecting element 26 of a device according to the invention, which may also be used in the device 1 instead of the connecting element 9. The connecting element 26 comprises a mandrel 27 with a three-way stopcock 28, with a first connection and a second connection being adjustable on the latter. In FIG. 4, the first connection of the three-way stopcock 28 has been set and, for setting the second connection, the three-way stopcock 28 is rotated further by 90° in a clockwise direction. In the interior of the connecting element 26, a first channel 29 and a second channel 30 extend across the three-way stopcock 28. In the first connection of the three-way stopcock 28, the first channel 29 connects the gas pressure device 14 to the gas phase container 10 and the second channel 30 connects the gas phase container 10 to the fluid container 7. In the second connection of the three-way stopcock 28, the first channel 29 connects the gas pressure device 14 to the fluid container 7 and the connection of the second channel 30 is interrupted by the three-way stopcock 28.

In the exemplary embodiment of a device of the invention according to FIG. 1 and FIG. 4, a method according to the invention is carried out wherein the pre-surgery preparation is started by draining the fluid 5 from the gas phase container 10 into the fluid container 7. Because of the draining, the fluid 5 is located in the fluid container 7 as intended for the surgery, and the second connection can be set at the three-way stopcock 28. The direct connection between the gas pressure device 14 and the fluid container 7, which thereby has been set, allows the gas phase container 10 and the connecting element 26 to be separated from each other. Furthermore, the fluid 5 can be provided at the surgical handpiece 3 at the irrigation pressure $P_I$ by charging the fluid container 7 with the initial pressure $P_A$. Also in this case, the volume of the gas phase 12 is reduced as in the exemplary embodiment according to FIG. 3, which advantageously lowers the inertia of the irrigation pressure control. As soon as the second connection has been set, the gas phase container 10 can be withdrawn from the mandrel 27.

Figure 5:
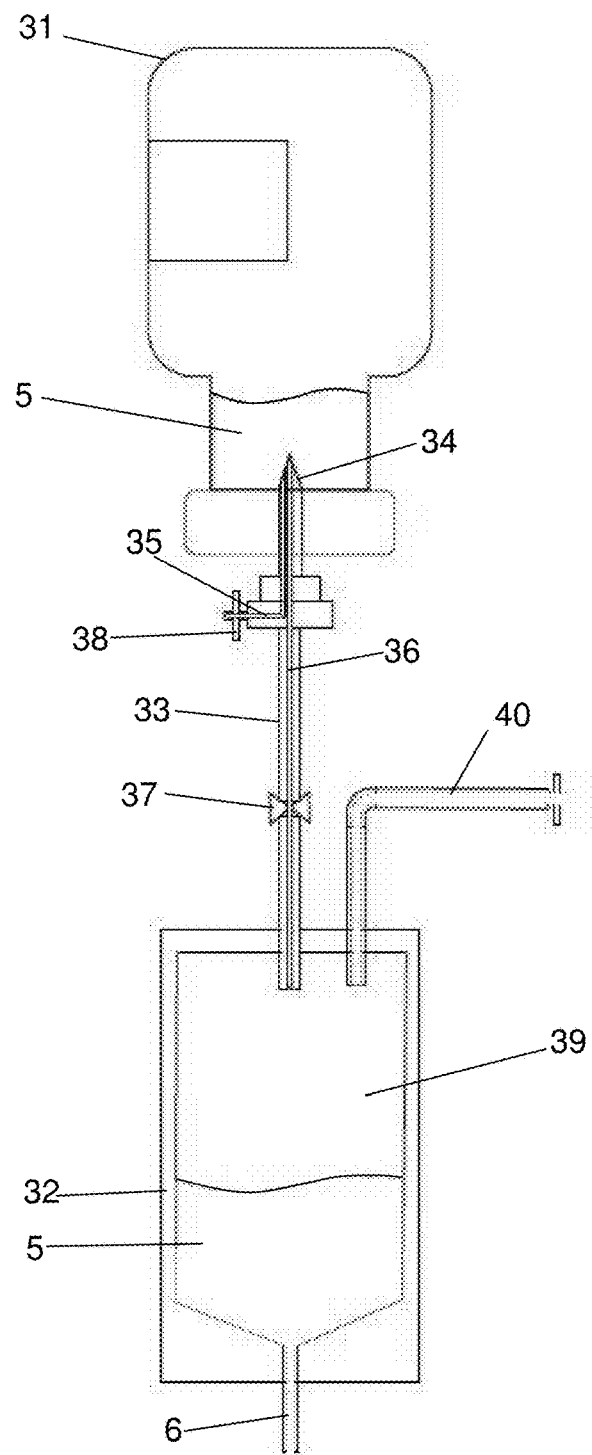
FIG. 5 shows a partial view of the establishment of a connection between a gas phase container and a fluid container comprising a fluid container line of a preferred exemplary embodiment of a device according to the invention.

FIG. 5 shows a partial view of a preferred exemplary embodiment of a device according to the invention, with the partial view depicting the establishment of a connection between a gas phase container 31 and a fluid container 32, which is applicable also in the device 1. The illustration shows a fluid level during the first procedural step according to the invention. The gas phase container 31 is suspended from an infusion holder, which is not illustrated, and is connected to the fluid container 32, which is also suspended from the infusion holder, via a connecting element 33. For this purpose, the connecting element 33 comprises a mandrel 34 by means of which the sealing of the gas phase container 31 is broken. For draining the fluid 5 from the gas phase container 31 into the fluid container 32, a first channel 35 and a second channel 36 are formed on the connecting element 33. The second channel 36 comprises a one-way valve 37 and connects the gas phase container 31 to the fluid container 32. The one-way valve 37 permits only one flow direction of liquids or gases, wherein, in said exemplary embodiment, the allowable flow direction runs from the gas phase container 31 toward the fluid container 32. The first channel 35 connects the gas phase container 31 with the surroundings thereof, whereby ambient air flows subsequently into the gas phase container 31 and a negative pressure is prevented in the gas phase container 31 when the fluid 5 is being drained into the fluid container 32. Furthermore, the first channel 35 exhibits a filter 38 which prevents the fluid 5 from being contaminated with dust particles from the ambient air. In order to provide the fluid 5 at a surgical handpiece at an irrigation pressure $P_I$, the surgical handpiece is connected to the fluid container 32 via the line 6. For controlling the irrigation pressure $P_I$ on the surgical handpiece, a gas phase 39 of the fluid container 32 is connected to a gas pressure device, which is not illustrated, via a fluid container line 40, which is part of line 13 according to FIG. 1. Because of the one-way valve 37, only the fluid container 32 is affected by changes in the initial pressure $P_A$ of the gas pressure device, and the gas phase container can be detached after the fluid 5 has been drained, or, respectively, the gas phase 39 affected by the pressure regulation enables a faster regulation of the irrigation pressure $P_I$ due to its size which has been restricted to the fluid container 32.

It may be mentioned that the connecting element instead of the one-way valve may exhibit an elastic spot in which the second channel is lockable by a clamp. Said clamp may be formed, for example, from a clamping ring, a spring-loaded clamping mechanism or other mechanisms which are applied in the field of medicine. In this way, the gas phase affected by the pressure regulation can be limited to the fluid container also without a one-way valve. In order to prevent the fluid container line from projecting into the fluid after the fluid has been drained, the fluid container has a larger volume than the gas phase container.

FIG. 1 and FIG. 5 show the device 1 during the pre-surgery preparation which consists essentially of the following procedural steps. The sealed gas phase container 31 is filled with the fluid 5 and is suspended from the infusion holder 8. During the pre-surgery preparation, the gas phase container 31 is connected to the fluid container 32 via the second channel 36 by means of the connecting element 33 and, furthermore, the gas pressure device 14 is connected to the fluid container 32 by the fluid container line 40. The former connection is established with the mandrel 34 by means of which the sealing of the gas phase container 31, which is not illustrated, is broken. For controlling the irrigation pressure $P_I$, the fluid 5 is started to be drained from the gas phase container 31 into the fluid container 32 according to the method of the invention. During the draining, the fluid container 32 is filled with the fluid 5 via the second channel 36, whereby the negative pressure emerging in the gas phase container 10 is equalized through the first gas-carrying channel 35. After the fluid 5 has been drained into the fluid container 32, the gas pressure device 14 is directly connected to the gas phase 39 and the fluid container 32 can be charged with the initial pressure $P_A$. The one-way valve 37 prevents the variable initial pressure $P_A$ from affecting also the gas phase container 31. Subsequently, the fluid 5 is made available at the surgical handpiece 3 at the irrigation pressure $P_I$. By means of the bidirectional regulation of the initial pressure $P_A$, the irrigation pressure $P_I$ can advantageously be increased or lowered particularly quickly, depending on the surgeon's requirement.

Figure 6:
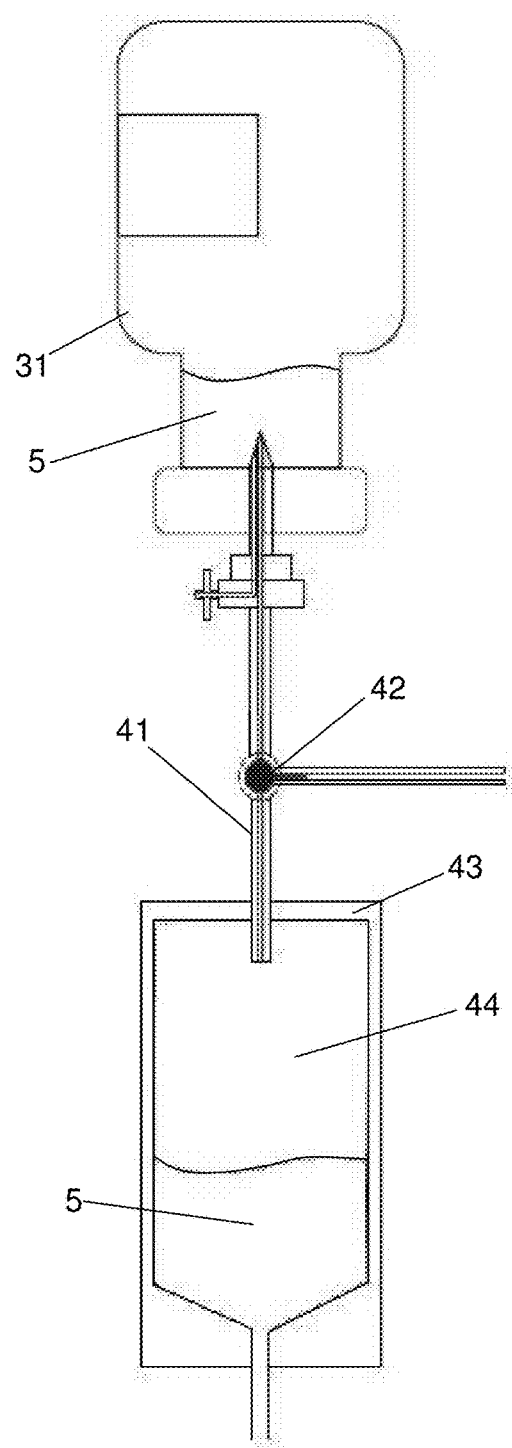
FIG. 6 shows a partial view of the establishment of a connection between a gas phase container and a fluid container of a device according to the invention, wherein a connecting element comprises a three-way stopcock.

FIG. 6 shows a partial view of an exemplary embodiment of a device according to the invention which, instead of the one-way valve of the exemplary embodiment according to FIG. 5, comprises a connecting element 41 with a three-way stopcock 42. On the three-way stopcock 42, a first connection or a second connection is adjustable, the first connection connecting the gas phase container 31 to a fluid container 43 and serving for draining the fluid 5 from the gas phase container 31 into the fluid container 43. The second connection connects a gas pressure device to a gas phase 44 of the fluid container 43, whereby the irrigation pressure $P_I$ of an eye surgery device is controllable and the fluid container line according to FIG. 5 can be omitted.

Figure 7:
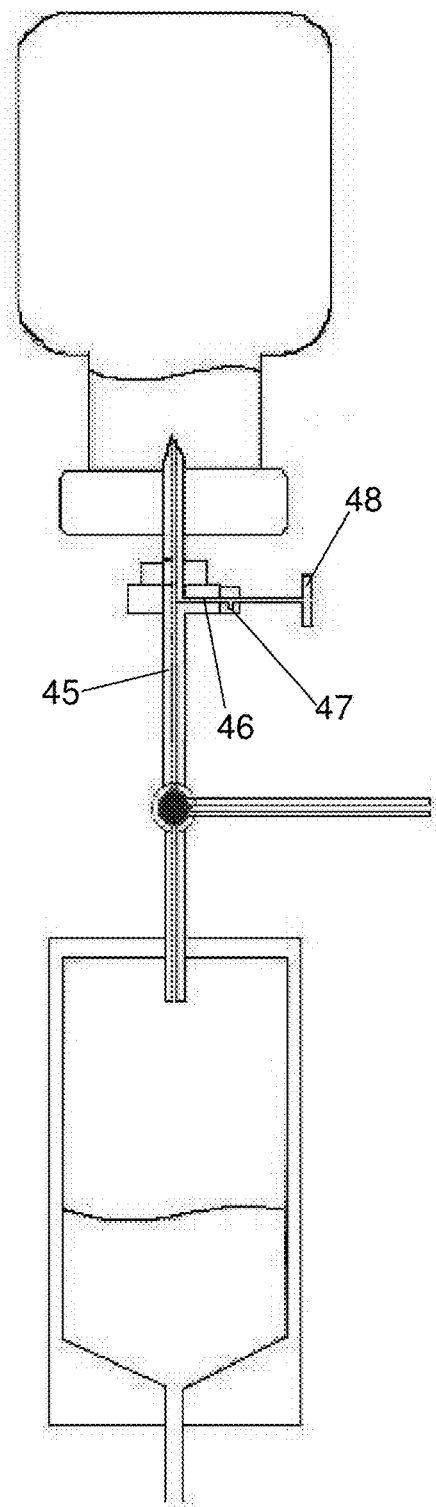
FIG. 7 shows a partial view of the establishment of a connection between a gas phase container and a fluid container of a device according to the invention, wherein a connecting element comprises a fluid deposition device.

FIG. 7 shows a partial view of a device according to the invention which, in addition to the exemplary embodiment according to FIG. 6, exhibits a fluid deposition device 47 in a connecting element 45 on a first channel 46. The fluid deposition device 47 makes sure that a filter 48 is not blocked or, respectively, subsequently clogged by fluid escaping through the second channel 46.

In the exemplary embodiments of the device according to the invention in accordance with FIG. 1 and FIG. 6 and, respectively, FIG. 7, the method according to the invention of preparing for surgery is in line with the specification according to FIG. 1 and FIG. 4.

In all six previously explained exemplary embodiments of the invention, the advantage is obtained that a very fast-reacting irrigation pressure control is achieved with means which are customary for surgical procedures, whereby an operation which is gentle to the eye is feasible for the surgeon by means of the devices.

The invention claimed is:

1. A device comprising a gas pressure device configured to provide a variable initial pressure ($P_A$), a fluid container configured to contain an eye rinse fluid, wherein the fluid container is connected to a surgical handpiece on a side which is lower in the operating position so as to be arranged to deliver the eye rinse fluid into the eye at an irrigation pressure ($P_I$), wherein the fluid container is connected to a connecting element on a side which is upper in the operating position, wherein the fluid container communicates with a gas phase container via a mandrel of the connecting element on a lower side of the gas phase container and wherein when the gas phase container and/or the fluid container exhibit(s) a gas phase, the gas phase communicates with the gas pressure device via the connecting element or a fluid container line, and the irrigation pressure ($P_I$) of the surgical handpiece is adjustable via the variable initial pressure ($P_A$) of the gas pressure device, wherein a first channel and a second channel are formed in the connecting element, wherein the gas phase container is connected with the surroundings thereof or to the gas pressure device via the first channel and wherein the second channel connects the gas phase container and the fluid container, and wherein the mandrel has an end projecting into the gas phase container, and wherein the first channel and the second channel, at the end of the mandrel, are extendible into the gas phase of the gas phase container during entire delivery of the eye rinse fluid into the eye.

2. The device according to claim 1, wherein the connection between the gas phase container and the surroundings thereof or the gas pressure device comprises a fluid deposition device configured and arranged to protect the gas pressure device from unwanted fluid entry.

3. The device according to claim 1, wherein the second channel comprises a one-way valve.

4. The device according to claim 1 further comprising a cover configured to cover the mandrel in order to connect the first channel to the second channel of the connecting element in a gastight manner.

5. The device according to claim 1, wherein the connecting element comprises a three-way stopcock that is configured to define a first connection and a second connection, wherein one of the first connection or the second connection is adjustable, wherein the first connection exists between the gas pressure device via the three-way stopcock, the gas phase container and the fluid container and wherein the second connection exists between the gas pressure device via the three-way stopcock and the fluid container.

6. The device according to claim 1, wherein the connecting element comprises a three-way stopcock that is configured to define a first connection and a second connection, wherein one of the first connection or the second connection is adjustable, wherein the first connection connects a gas phase container to the fluid container and wherein the second connection connects a gas pressure device to the fluid container.

7. The device according to claim 1, wherein the fluid container comprises an infusion bag.

8. The device according to claim 1, wherein the gas phase container is a bottle configured to hold a saline solution.

9. A method of providing the eye rinse fluid at the surgical handpiece on the device according to any of the preceding claims, wherein the following acts are performed:
draining essentially all of the eye rinse fluid from the gas phase container into the fluid container;
charging the fluid container with the initial pressure ($P_A$); and
providing the eye rinse fluid at the surgical handpiece at the irrigation pressure ($P_I$) adjustable by the surgeon.

10. The method according to claim 9, wherein the gas phase container is separated from the connecting element and the connecting element is covered with a cover before the fluid container is charged with the initial pressure ($P_A$).

11. The method according to claim 9, wherein the second connection is set on the three-way stopcock and the gas phase container is fluidly isolated from the connecting element before the fluid container is charged with the initial pressure ($P_A$).

* * * * *